United States Patent [19]

Tung et al.

[11] Patent Number: 4,585,854

[45] Date of Patent: Apr. 29, 1986

[54] POLYESTER COMPOSITION

[75] Inventors: William C. T. Tung, Tallmadge; George A. Deisz, Akron, both of Ohio

[73] Assignee: The Goodyear Tire & Rubber Company, Akron, Ohio

[21] Appl. No.: 699,286

[22] Filed: Feb. 7, 1985

Related U.S. Application Data

[62] Division of Ser. No. 600,862, Apr. 16, 1984, Pat. No. 4,525,524.

[51] Int. Cl.[4] .............................................. C08G 63/68

[52] U.S. Cl. .................................... 528/295; 528/302; 528/305; 528/308

[58] Field of Search ................ 528/295, 302, 305, 308

[56] References Cited

U.S. PATENT DOCUMENTS

| | | | |
|---|---|---|---|
| 3,563,942 | 2/1971 | Heiberger | 524/603 X |
| 4,257,928 | 3/1981 | Vachon et al. | 528/302 X |
| 4,483,976 | 11/1984 | Yamamoto et al. | 528/295 |
| 4,499,262 | 2/1985 | Fagerburg et al. | 528/295 X |

*Primary Examiner*—Lucille M. Phynes
*Attorney, Agent, or Firm*—Alvin T. Rockhill

[57] ABSTRACT

Polyester compositions which are dispersible or soluble in water based systems can be very valuable as adhesives, coatings, paints, and the like. The use of water based solvent systems eliminates recovery and toxicity problems normally related with many organic solvents. The polyester compositions of this invention have an increased affinity for water based systems by the incorporation therein salts of organic sulfonic acid monomers and by carboxyl terminating these polyesters to a very substantial degree. The water based systems in which these modified polyesters are useful contain an alcohol in addition to water.

13 Claims, No Drawings

POLYESTER COMPOSITION

This is a divisional, of application Ser. No. 600,862, filed on Apr. 16, 1984 (now issued as U.S. Pat. No. 4,525,524).

BACKGROUND OF THE INVENTION

Organic solvent based polyester resins have been used in a variety of applications, including coatings, paints, adhesives, and the like. Many organic solvents commonly used in conjunction with such polyester resins present environmental problems associated with their toxicity. There has been a growing interest in the use of aqueous based polyester compositions as a means of eliminating toxicity problems and complying with certain government standards and regulations.

Various water dispersible polyester resins are known in the art. U.S. Pat. No. 4,179,420 discloses water dispersible oil-modified polyesters and oil-free polyesters which are formed by the reaction of aromatic dicarboxylic acids, aliphatic dicarboxylic acids, and polyols. This reference indicates that maleic anhydride or trimellitic anhydride can be used to form polyesters which can become water-soluble with the polyesters produced from these reactants being rendered water-soluble by the aid of an amine, a metal oxide, hydroxide or carbonate. U.S. Pat. No. 4,304,900 and 4,304,901 relate to linear water dissipatible polyesters and polyester amides which contain a disulfonamido compound and a sulfonic acid salt moiety, respectively, in order to render them water-dissipatible.

SUMMARY OF THE INVENTION

The polyesters of this invention are very useful since they are soluble or dispersible in water based systems. It is not envisioned that the polyesters of this invention will normally be utilized in aqueous solvent systems that contain nothing but water. This is because pure water (water that does not contain significant amounts of other materials) is not a very good solvent for the polyesters of this invention. However, water based systems that contain alcohols which contain from 3 to 5 carbon atoms work very well as solvents for the polyester compositions of this invention.

This invention reveals a polyester comprised of repeat units which are derived from (a) a diacid component which is comprised of (1) from 20 to 90 mole percent of at least one member selected from the group consisting of dimethylterephthalate and terephthalic acid, (2) from 1 to 6 mole percent of at least one salt of an organic sulfonic acid monomer and (3) from 4 to 74 mole percent of at least one member selected from the group consisting of alkyl dicarboxylic acids having from 4 to 36 carbon atoms, diesters of alkyl dicarboxylic acids having from 6 to 38 carbon atoms, aryl dicarboxylic acids having from 9 to 20 carbon atoms, diesters of aryl dicarboxylic acids having from 11 to 22 carbon atoms, alkyl substituted aryl dicarboxylic acids having from 9 to 20 carbon atoms, diesters of alkyl substituted aryl dicarboxylic acids having from 11 to 22 carbon atoms, dimethylorthophthalate, dimethylisophthalate, orthophthalic acid, and isophthalic acid: and (b) a diol component which is comprised of (1) from 20 to 100 mole percent ethylene glycol, and (2) from 0 to 80 mole percent of one or more members selected from the group consisting of glycols having from 3 to 12 carbon atoms and glycol ethers having from 4 to 12 carbon atoms: wherein said polyester is terminated with carboxyl end groups. These polyesters are dispersible and/or soluble in water/alcohol systems.

This invention also reveals a liquid system comprised of: (A) a water/alcohol solvent comprised of from 50 to 80 weight percent water and from 20 to 50 weight percent of at least one alcohol having from 3 to 5 carbon atoms: and (B) a polyester composition comprised of repeat units which are derived from (a) a diacid component which is comprised of (1) from 20 to 90 mole percent of at least one member selected from the group consisting of dimethylterephthalate and terephthalic acid, (2) from 1 to 6 mole percent of at least one salt of an organic sulfonic acid monomer, and (3) from 4 to 74 mole percent of at least one member selected from the group consisting of alkyl dicarboxylic acids having from 4 to 36 carbon atoms, diesters of alkyl dicarboxylic acids having from 6 to 36 carbon atoms, aryl dicarboxylic acids having from 9 to 20 carbon atoms, diesters of aryl dicarboxylic acids having from 11 to 22 carbon atoms, alkyl substituted aryl dicarboxylic acids having from 9 to 22 carbon atoms, diesters of alkyl substituted aryl dicarboxylic acids having from 11 to 20 carbon atoms, dimethylorthophthalate, dimethylisophthalate, orthophthalic acid, and isophthalic acids; and (b) a diol component which is comprised of (1) from 20 to 100 mole percent ethylene glycol, and (2) from 0 to 80 mole percent of one or more members selected from the group consisting of glycols having from 3 to 12 carbon atoms and glycol ethers having from 4 to 12 carbon atoms; wherein said polyester is terminated with carboxyl end groups: and wherein said liquid system has a pH of at least 7.

DETAILED DESCRIPTION OF THE INVENTION

The polyester compositions of this invention are prepared by reacting a diacid component with a diol component. This diacid component can, of course, be a diester, such as dimethylterephthalate. Thus, the polyester compositions formed are comprised of repeat units which are derived from diacid components and diol components. These polyester compositions can be made in any conventional manner well known in the art. Thus, conventional temperatures, catalysts, amounts of catalysts, stabilizers, and the like, are utilized as known to the art or literature. Moreover, when an acid is utilized, as a starting material in contrast to an ester, the polymer can be prepared in a manner as set forth and described in U.S. Pat. No. 4,020,049 to Rinehart, which is hereby fully incorporated by reference in its entirety with regard to a method of making a polyester.

The diacid component used in the preparation of these polyesters is comprised of (1) from 20 to 90 mole percent (based upon total diacids) of dimethylterephthalate and/or terephthalic acid, (2) from 1 to 6 mole percent of one or more salts of organic sulfonic acid monomers, and (3) from 4 to 74 mole percent of one or more members selected from the group consisting of alkyl dicarboxylic acids having from 4 to 36 carbon atoms, diesters of alkyl dicarboxylic acids having from 6 to 38 carbon atoms, aryl dicarboxylic acids having from 9 to 20 carbon atoms, diesters of aryl dicarboxylic acids having from 11 to 22 carbon atoms, alkyl substituted aryl dicarboxylic acids having from 9 to 20 carbon atoms, diesters of alkyl substituted aryl dicarboxylic acids having from 11 to 22 carbon atoms, dimethylorthophthalate, dimethylisophthalate, orthophthalic acid, and isophthalic acid.

The organic sulfonic acid monomers which are polymerized into the polyesters of this invention increase the affinity of the polyester for water/alcohol systems. These organic sulfonic acid monomers will generally contain two carboxyl groups (—COOH). When the organic sulfonic acid monomer employed contains only one carboxyl group, it functions as a chain-terminating agent and limits the molecular weight of the polyester. In order to compensate for this, a branching agent that contains three or more esterifiable groups can be employed. On the other hand, organic sulfonic acid monomers which contain 3 or more carboxyl groups can also be employed. Such organic sulfonic acids which contain 3 or more carboxyl groups will act as chain branching agents.

The organic sulfonic acid monomers used in the practice of this invention are substituted carboxylic acids. As has been pointed out these sulfonic acid salts are generally substituted dicarboxylic acids. The sulfonic acid salt substituent in these organic sulfonic acid monomers have the structural formula:

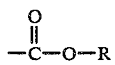

wherein M is an alkali metal or ammonium. Normally, M will be sodium, lithium, potassium, calcium, or ammonium. Thus, these organic sulfonic acid monomers are hydrocarbons which are substituted with at least one sulfonic acid salt substituent and at least one carboxyl group. These hydrocarbons include aliphatic, cycloaliphatic, and aromatic (including aromatic and cycloaliphatic substituted aromatic and aromatic substituted aliphatic and cycloaliphatic) hydrocarbons. Alkyl ester groups can be used in place of the carboxyl groups in these organic sulfonic acid monomers. Such alkyl ester groups have the structural formula:

—C(=O)—O—R wherein R is an alkyl group which will normally contain from 1 to 10 carbon atoms, which will preferably contain from 1 to 5 carbon atoms, and which will most preferably contain 1 carbon atom.

The preferred organic sulfonic acid monomers for use in this invention are aromatic carboxylic acids containing a sulfonic acid salt substituent. These sulfonic acid salt substituted aromatic carboxylic acids contain at least one sulfonic acid salt substituent and at least one carboxyl group. These substituted aromatic carboxylic acids can be presented by the structural formula:

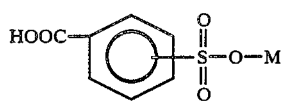

wherein the sulfonic acid salt substituent can be in the ortho, meta, or para position.

The most preferred organic sulfonic acid salt monomers for incorporation into the polyesters of this invention are alkali salts of sulfo phthalates and alkali salts of sulfo alkyl phthalates. Alkali salts of sulfo phthalates have the general structural formula:

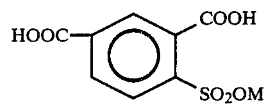

wherein the sulfo salt substituent can be in the ortho, metal, or para position and wherein the phthalate can be orthophthalic acid, isophthalic acid or terephthalic acid. The most preferred salt of a sulfo phthalate is the sodium salt of 5-sulfo-1,3-benzene dicarboxylic-acid which has the structural formula:

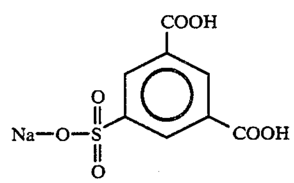

The slats of sulfo alkyl phthalates which promote resin or polymer solubility in water/alcohol solvent systems have alkyl groups which normally contain from 1 to 5 carbon atoms, with methyl groups being the preferred alkyl moiety. Although lithium, potassium, ammonium, and calcium salts can be utilized, the sodium salt of sulfo alkyl phthalates is preferred. Salts of sulfo alkyl isophthalate are preferred for incorporation into the polyester compositions of this invention. The sodium salt of 5-sulfo-1,3-benzene dicarboxylic-acid-1,3-dimethylester has the structural formula:

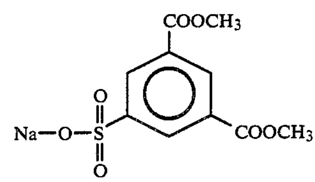

Good polyester composition solubility or dispersible in water/alcohol systems can be obtained by utilizing from 1 to 6 mole percent and preferably from 2 to 4 mole percent of the organic sulfonic acid salt monomer based upon the total amount of the acid or ester therein.

The diacid component also contains at least one member selected from the group consisting of alkyl dicarboxylic acids, diesters of alkyl dicarboxylic acids, aryl dicarboxylic acids, diesters of aryl dicarboxylic acids, alkyl substituted aryl dicarboxylic acids, diesters of alkyl substituted aryl dicarboxylic acids, dimethylorthophthalate, dimethylisophthalate, orthophthalic acid, and isophthalic acid. The alkyl dicarboxylic acids contain from 4 to 36 carbon atoms and preferably from 4 to 12 carbon atoms. Some representative examples of such alkyl dicarboxylic acids include glutaric acid, adipic acid, pimelic acid, and the like. The various diesters of the dialkyl dicarboxylic acids normally contain from 6 to 36 carbon atoms and preferably from 6 to 12 carbon atoms. A representative example of such a diester of an alkyl dicarboxylic acid is azelaic acid. The aryl dicarboxylic acids which can be utilized in the diacid component normally contain from 9 to 20 carbon atoms and preferably from 9 to 16 carbon atoms. The diesters of aryl dicarboxylic acids which can be utilized contain from 11 to 22 carbon atoms and preferably from 11 to 15 carbon atoms. Some representative examples of diesters of aryl dicarboxylic acids include diethylterephthalate, diethylisophthalate, diethylorthophthalate, dimethylnaphthalate, diethylnaphthalate, and the like. The alkyl substituted aryl dicarboxylic acids which can be utilized have from 9 to 20 carbon atoms and preferably from 9 to 16 carbon atoms. The diesters of alkyl substituted aryl dicarboxylic acids which can be employed in the diacid component contain from 11 to 22 carbon atoms and preferably from 11 to 15 carbon atoms.

The diol component used in the preparation of the polyester compositions of this invention is comprised of from 20 to 100 mole percent of ethylene glycol and from 0 to 80 mole percent of one or more members selected from the group consisting of glycols having from 3 to 12 carbon atoms and glycol ethers containing from 4 to 12 carbon atoms. Thus, the diol component can be totally ethylene glycol. It is preferred for the diol component to contain from 50 to 100 mole percent ethylene glycol and from 0 to 50 mole percent of one or more members selected from the group consisting of glycols having from 3 to 12 carbon atoms and glycol ethers containing from 4 to 12 carbon atoms. However, up to 80 mole percent of other glycols and glycol ethers can be employed. In cases where glycols in addition to ethylene glycol are utilized it is preferable for them to contain from 3 to 8 carbon atoms. In cases where glycol ethers are utilized in conjunction with ethylene glycol in the diol component it is preferable for them to contain from 4 to 8 carbon atoms. Some representative examples of glycols that can be used in conjunction with ethylene glycol include 1,3-propylene glycol, 1,2-propylene glycol, 2-2-diethyl-1,3-propanediol, 2,2-dimethyl-1,3-propanediol, 2-ethyl-2-butyl-1,3-propanediol, 2-ethyl-2-isobutyl-1,3-propanediol, 1,3-butanediol, 1,4-butanediol, 1,5-pentanediol, 1,6-hexanediol, 2,2,4-trimethyl-1,6-hexanediol, 1,3-cyclohexanedimethanol, 1,4-cyclohexanedimethanol, and 2,2,4,4-tetramethyl-1,3-cyclobutanediol.

If branching is desirable then it will be advantageous to use a branching agent in the polyesterification reaction. This may be the case if an organic sulfonic acid monomer is utilized which is a monocarboxylic acid. Such branching agents may contain three or more functional groups and they preferably contain three or four functional groups. The reactive groups may be carboxyl or aliphatic hydroxyl. The branching agent may contain both types of groups. Examples of acidic branching agents include trimesic acid, trimellitic acid, pyromellitic acid, butanetetracarboxylic acid, naphthalene tricarboxylic acids and cyclohexane-1,3,5-tricarboxylic acid. Examples of hydroxyl branching agents (polyols) include glycerin, trimethylolpropane, pentaerythritol, dipentaerythritol, 1,2,6-hexanetriol and 1,3,5-trimethylolbenzene. Examples of hydroxy acids are 2,2-dihydroxymethyl propionic acid; 10,11 dihydroxyundecanoic acid; and 5-(2-hydroxyethoxy)isophthalic acid. Generally from 0 to 3 percent of a polyol containing from 3 to 12 carbon atoms will be used as the branching agent (based upon the total diol component).

In the preparation of the polyester compositions of this invention the mole ratio of the total amount of diols charged to the total amount of diacids generally ranges from at least about 1.0 to about 2.2, and preferably from 1.5 to 2.2. In other words, the excess of the total amount of diols utilized to the total amount of acids or diesters thereof is generally approximately 2.

The polyester compositions of this invention normally have a relatively low molecular weight ranging from 1,000 to 7,000. More preferably they have molecular weights ranging from 2,000 to 5,000. Polyester compositions of this type and molecular weight can be prepared by utilizing polymerization techniques well known to those skilled in the art, such as by utilizing short polymerization times.

The polyester compositions of this invention have their polymer chains terminated with carboxyl end groups. These polyesters are very substantially carboxyl terminated with almost every polymer chain having 1 to 4 carboxyl groups at both of its chain ends. In most cases the polyesters of this invention will have chain ends that are terminated with two carboxyl groups. Such carboxyl termination can be achieved by utilizing any acid anhydride having from 4 to about 20 carbon atoms during the $S_3$ stage. That is, the acid anhydride is added after the condensation reaction (the $S_2$ stage) in which a vacuum is gradually applied until a minimum vacuum has been reached, at which point commences the $S_3$ stage, that is the vacuum is held and the condensation continued. Desirably, the anhydride is added at the late $S_3$ stage. Some representative examples of suitable acid anhydrides include trimellitic anhydride, succinic anhydride, phthalic anhydride, and the like, with trimellitic anhydride being greatly preferred. The employment of trimellitic anhydride will result in the polyester chains being terminated (capped) with two carboxyl groups at each end. The amount of the acid anhydride which will be utilized ranges from about 1 to 6 mole percent of the total molar amount of diacid components utilized in the polyester, and preferably from 2 to 4 mole percent. Other techniques which will result in substantial carboxyl termination of the polyester can also be employed.

The polyesters of this invention are dispersible and/or soluble in water/alcohol solutions. Water will not work well alone as a solvent for these polyesters and neither will alcohols. The water/alcohol systems which are used as solvents generally contain from about 50 to about 80 weight percent water and from about 20 to about 50 weight percent alcohol. These water/alcohol systems are slightly basic having a pH of at least 7. Thus, small amounts of various bases are added, for example, sodium hydroxide or ammonium hydroxide, in order to raise the pH of the system to at least 7. It is desirable for these water/alcohol systems to be basic in order to neutralize the acid groups on the polyester converting them into salts. Liquid systems containing water, an alcohol, and the polyester will generally have a pH in the range of 7 to 9. It will normally be preferred for such liquid systems to have a pH in the range of 7 to 8. The pH of these liquid systems can be easily adjusted to within the range of 7 to 8 by the addition of an adequate amount of ammonium hydroxide.

These water based solvent systems can contain up to about 60 weight percent of the polyester. Thus, such liquid systems which are comprised of water, an alcohol, and the polyester normally contain from 1 to 60 weight percent of the polyster based upon the total weight of the liquid system. The liquid systems of this invention will preferably contain from about 5 to about 40 weight percent of the polyester based upon the total weight of the liquid system, and will most preferably contain from 10 to 30 weight percent of the polyester.

The alcohols used in these liquid systems contain from 3 to 5 carbon atoms. Some representative examples of alcohols that can be used in such liquid systems include: n-propyl alcohol, isopropyl alcohol, n-butyl alcohol, isobutyl alcohol, t-butyl alcohol, n-pentyl alcohol, isopentyl alcohol, s-pentyl alcohol and t-pentyl alcohol. Isopropyl alcohol, n-butanol, n-proyl alcohol, t-butyl alcohol and s-butyl alcohol are greatly preferred for use as the alcohol in the liquid systems of this invention.

The water based liquid systems of this invention can be applied to a variety of substrates for use in paints, and coatings. Examples of specific uses include either spray or brush applications as to plastic and metal substrates and the like. Various conventional dyes, pigments, and colorants can be utilized in various amounts to impart a desired color to the polyester composition whenever a particular color is desired to be imparted to the object coated or painted. The polyesters of this invention can also be employed as a resin for ink. The polyester solutions of this invention can also be used as adhesives. One big advantage to using such liquid systems as adhesives is that they are not water soluble and thus can be used in applications where they are exposed to water. They are particularly useful for adhering aluminum foils to poyethyene terephthalate films. They can also be utilized in a wide variety of other types of laminations and as a primer for polyethylene terephthalate articles so that they will more readily accept printers ink.

The liquid systems of this invention can also be used as hair-spray. Such hair-spray will normally contain from 1 to 10 weight percent polyester and preferably from 2 to 5 weight percent based upon the total weight of the liquid system. Liquid systems of this type which are used as hair-spray can also contain a perfume to impart a pleasing scent or fragrant odor to the spray.

Since the polyesters of this invention are not soluble in water this hair-spray will not be washed out of hair by water. Thus, hair which is set with this hair-spray will remain in place even after being "rained on" since the polyester which acts as an adhesive will not be washed out. However, the polyester can be easily washed out of the hair by using a solution of isopropyl alcohol and water or soap (shampoo) and water.

This invention is illustrated by the following examples which are merely for the purpose of illustration and are not to be regarded as limiting the scope of the invention or the manner in which it may be practiced. Unless specifically indicated otherwise, parts and percentages are given by weight.

EXAMPLE 1

5.7 pounds of dimethylterephthalate, 3.6 pounds of ethylene glycol, 2.45 pounds of neopentyl glycol, and 205 grams of dimethyl sodium sulfo isophthalate were charged into a polymerization reactor utilizing zinc acetate as the catalyst. The transesterification reaction was carried out at 180° to 200° C. When the theoretical amount of methanol was distilled over 1.37 pounds of isophthalic acid and 2.8 pounds of azelaic acid were added. The mixture was allowed to react at about 230° C. for 40 minutes under a nitrogen atmosphere. The pressure was then reduced gradually to about 0.1 millimeter of mercury and the temperature was gradually raised to about 260° C. This polymerization reaction was carried out for about one hour with $Sb_2O_3$ as the catalyst. The reactor was then pressurized and cooled to a temperature of 210° to 220° C. 206 grams of trimellitic anhydride was added to the reaction mixture and was stirred under a nitrogen atmosphere for about 30 minutes at a temperature of 210° C. The final product was discharged and determined to have an intrinsic viscosity of 0.326 and a glass transition temperature (Tg) of 20° C.

This polyester was readily solvated into a water/alcohol mixture containing 100 parts of isopropanol, 300 parts of water, and 3 parts of ammonium hydroxide. This liquid system could be employed as an adhesive for a variety of purposes.

EXAMPLE 2

The same procedure that was specified in Example 1 was utilized in this experiment except that the acid component of the polyester contained 43.1% dimethyl terephthalate, 2.9% dimethyl sodium sulfo isophthalate, 50.9% isophthalic acid, and 3.2% trimellitic anhydride and the diol component contained 27% neopentyl glycol and 73% ethylene glycol. The polyester produced had an intrinsic viscosity of 0.25 and a glass transition temperature of 64° C. This polyester was also readily solvated in the water based solvent system described in Example 1.

EXAMPLE 3

The same procedure that was utilized in Example 1 was employed in this experiment except that ethylene glycol was the only diol component utilized with the acid component being a mixture of 34.2 mole % dimethylterephthalate, 17.8% isophthalic acid, 41.7% azelaic acid, 2.8% dimethyl sodium sulfo isophthalate, and 3.5% trimellitic anhydride. The polyester produced had an intrinsic viscosity of 0.3 and had a glass transition temperature of −8° C. It was also readily solvated in the water/alcohol solvent system described in Example 1.

EXAMPLE 4

The same procedure that was specified in Example 1 was utilized in this experiment except that the acid component of the polyester contained 45.2 mole percent dimethyl terephthalate, 2.7 mole percent dimethyl sodium sulfo isophthalate, 32.2 mole percent isophthalic acid, 15.7 mole percent azelaic acid, and 4.2 mole percent trimellitic anhydride and the diol component contained 73.7 mole percent ethylene glycol and 26.3 mole percent neopentyl glycol. The resultant polymer had an intrinsic viscosity of 0.3 and a glass transition temperature of 35° C. This polymer was also solvated in the water/alcohol solution described in Example 1. These examples clearly show that the polyester compositions of this invention are soluble or dispersible in water based solvents containing a mixture of water and alcohol.

While certain representative embodiments and details have been shown for the purpose of illustrating the invention, it will be apparent to those skilled in this art that various changes and modifications may be made therein without departing from the scope of the invention.

What is claimed is:

1. A polyester comprised of repeat units which are derived from (A) a diacid component which is comprised of (1) from 20 to 90 mole percent of at least one member selected from the group consisting of dimethylterephthalate and terephthalic acid, (2) from 1 to 6 mole percent of at least one salt of an organic sulfonic acid monomer, and (3) from 4 to 74 mole percent of at least one member selected from the group consisting of alkyl dicarboxylic acids having from 4 to 36 carbon atoms, diesters of alkyl dicarboxylic acids having from 6 to 38 carbon atoms, aryl dicarboxylic acids having from 9 to 20 carbon atoms, diesters of aryl dicarboxylic acids having from 11 to 22 carbon atoms, alkyl substituted aryl dicarboxylic acids having from 9 to 20 carbon atoms, diesters of alkyl substituted aryl dicarboxylic acids having from 11 to 22 carbon atoms, dimethylorthophthalate, dimethylisophthalate, orthophthalic acid, and isophthalic acid: and (B) a diol component which is comprised of (1) from 20 to 100 mole percent ethylene glycol, and (2) from 0 to 80 mole percent of one or more members selected from the group consisting of glycols having from 3 to 12 carbon atoms and glycol ethers having from 4 to 12 carbon atoms: wherein said polyester is terminated with carboxyl end groups.

2. A polyester as specified in claim 1 wherein said salt of an organic sulfonic acid monomer is an alkali salt of a sulfo dialkyl isophthalate or an alkali salt of a sulfo isophthalatic acid.

3. A polyester as specified in claim 2 wherein said alkali salt of a sulfo dialkyl isophthalate is a sodium salt of sulfo dimethyl isophthalate.

4. A polyester as specified in claim 2 wherein said polyester is terminated with 2 carboxyl end groups at said polyesters chain ends.

5. A polyester as specified in claim 4 wherein said polyester is carboxyl terminated with trimellitic anhydride.

6. A polyester as specified in claim 2 wherein said diol component is comprised of (1) from 50 to 100 mole percent ethylene glycol and (2) from 0 to 50 mole percent of one or more members selected from the group consisting of glycols having from 3 to 12 carbon atoms and glycol ethers having from 4 to 12 carbon atoms.

7. A polyester as specified in claim 6 wherein said members selected from the group consisting of glycols having from 3 to 12 carbon atoms and glycol ethers having from 4 to 12 carbon atoms are glycols having from 3 to 8 carbon atoms and glycol ethers having from 4 to 8 carbon atoms.

8. A polyester as specified in claim 6 wherein said members selected from the group consisting of glycols having from 3 to 12 carbon atoms and glycol ethers having from 4 to 12 carbon atoms are selected from the group consisting of 1,3-propylene glycol, 1,2-propylene glycol, 2,2-diethyl-1,3-propanediol, 2,2-dimethyl-1,3-propanediol, 2-ethyl-2-butyl-1,3-propanediol, 2-ethyl-2-isobutyl-1,3propanediol, 1,3butanediol, 1,4-butanediol, 1,5-pentanediol, 1,6-hexandeiol, 2,2,4-trimethyl-1,6-hexanediol, 1,3-cyclohexanedimethanol, 1,4-cyclohexanedimethanol, and 2,2,4,4-tetramethyl-1,3-cyclobutanediol.

9. A polyester as specified in claim 3 wherein said diol component is ethylene glycol.

10. A polyester as specified in claim 1 wherein said polyester has a molecular weight of about 1000 to about 7000.

11. A polyester as specified in claim 6 wherein said polyester has a molecular weight of about 1000 to about 7000.

12. A polyester as specified in claim 6 wherein said members selected from the group consisting of alkyl dicarboxylic acids having from 4 to 20 carbon atoms, diesters of alkyl dicarboxylic acids having from 6 to 20 carbon atoms, aryl dicarboxylic acids having from 9 to 20 carbon atoms, diesters of aryl dicarboxylic acids having 11 to 20 carbon atoms, alkyl substituted aryl dicarboxylic acids having from 9 to 20 carbon atoms, diesters of alkyl substituted aryl dicarboxylic acids having from 11 to 20 carbon atoms, dimethylorthopthalate, dimethylisophthalate, orthopthalic acid, and isophthalic acid are selected from the group consisting of isophthalic acid and azelaic acid and wherein said diol component is comprised of from 50 to 100 mole percent ethylene glycol and from 0 to 50 mole percent neopentyl glycol.

13. A polyester as specified in claim 12 wherein said polyester has a molecular weight of 2000 to 5000.

* * * * *